United States Patent [19]

Hirai

[11] 4,299,244
[45] Nov. 10, 1981

[54] ENDOSCOPE WASHING APPARATUS

[76] Inventor: Jin Hirai, No. 2852 Yutaka-cho, Hamanmatsu City, Shizuoaka Prefecture, Japan

[21] Appl. No.: 63,331

[22] Filed: Aug. 2, 1979

[51] Int. Cl.$^3$ .......................... B08B 3/04; B08B 9/02; B08B 11/02
[52] U.S. Cl. .............................. 134/102; 134/166 C; 134/170; 134/171; 134/199
[58] Field of Search ............... 134/94, 99, 102, 166 R, 134/166 C, 170-171, 182, 184, 198-199, 201, 22 C; 422/1; 239/398, 418

[56] References Cited

U.S. PATENT DOCUMENTS

| | | | |
|---|---|---|---|
| 1,684,047 | 9/1928 | Stoven | 134/199 X |
| 2,136,158 | 11/1938 | Thomas | 134/199 UX |
| 2,536,843 | 1/1951 | Dye | 134/199 X |
| 3,657,990 | 4/1972 | Wilhelm | 134/102 |
| 3,963,438 | 6/1976 | Banez | 134/22 C X |
| 4,064,886 | 12/1977 | Heckele | 134/171 X |

FOREIGN PATENT DOCUMENTS

| | | | |
|---|---|---|---|
| 246323 | 8/1963 | Australia | 134/22 C |
| 816910 | 7/1959 | United Kingdom | 134/102 |

Primary Examiner—Robert L. Bleutge
Attorney, Agent, or Firm—Haseltine and Lake

[57] ABSTRACT

An endoscope washing apparatus in which the optical-fiber tube of an endoscope is submerged in flowing water into which a multiplicity of air streams are injected to produce a myriad of foams, which impinge upon the outer peripheral surface of the tube for removing contaminants or stains from the surface in cooperation with the flow of water. By preference, water may be passed through the conduits in the optical-fiber tube and further through the conduits in a light-guide tube of the endoscope and, subsequently, the optical-fiber tube and the conduits in the optical-fiber and light-guide tubes may be treated with a disinfectant or sterilizing solution.

23 Claims, 6 Drawing Figures

ENDOSCOPE WASHING APPARATUS

FIELD OF THE INVENTION

The present invention relates to an apparatus for cleaning an endoscope and, more particularly, to an endoscope washing apparatus for washing, sterilizing, rinsing and drying an endoscope which is used for the biopsy of an internal organ of human body.

BACKGROUND OF THE INVENTION

Endoscopes play a vital role for the visual examination and photographing of the cavities of internal organs of human body and the extraction of cellular tissues or other objects from the internal organs and, thus, various improvements have been made in endoscopes to enhance the performance efficiency, manoeuverability and durability of the endoscopes. As is well known in the art, an endoscope is a fiberscope using a flexible optical-fiber tube having various optical and biopsy elements attached to or incorporated in the leading end portion of the tube. During use of the endoscope, the optical-fiber tube of the endoscope is inserted into the cavity of the organ to be examined and is manipulated to move in various directions within the cavity of the organ from the manipulator unit to which the optical-fiber tube is fitted. The optical-fiber tube of an endoscope is, thus, subject to contamination with various foreign substances such as blood and other humors and, for this reason, must be washed and sterilized after each use of the endoscope. A washing apparatus tailored to endoscopes in general is therefore furnished and used where endoscopes are put to use in a hospital, clinic, infirmary or ambulance. Conventional washing apparatus for endoscopes are, however, becoming obsolescent for the endoscopes being improved at fast tempo.

A conventional endoscope washing apparatus uses a spray nozzle through which water or any disinfectant or sterilizing solution is to be sprayed onto the outer peripheral surface of the optical-fiber tube. The spray nozzle of the prior-art endoscope washing apparatus is arranged to discharge a stream of water or the disinfectant or sterilizing solution at a predetermined angle to the outer peripheral surface of the optical-fiber tube held in a predetermined position with respect to the optical-fiber tube. The spray nozzle thus arranged is moved along the optical-fiber tube from the vicinity of one end of the tube to the vicinity of the other end of the tube so that the optical-fiber tube contaminated is washed or sterilized throughout the length of the tube. One of the drawbacks inherent in an endoscope washing apparatus of this nature is that, if the optical-fiber tube of the endoscope to be treated by the washing apparatus has in its leading end portion an opening or corner which is angled with respect to the direction in which a stream of liquid is to be discharged from the spray nozzle, the stream of the liquid ejected from the nozzle is not permitted to reach such an opening or corner so that, if there is a mucous or solid substance deposited in the opening or corner, the substance can not be removed satisfactorily from the tube. Another problem encountered in a prior-art endoscope washing apparatus using a spray nozzle is that the washing apparatus is of no use for the cleaning of the passageways formed in the optical-fiber tube of an endoscope in which various conduits are incorporated in the optical-fiber tube for conducting water, air under pressure and suction therethrough and passing the wires connected to the forceps carried in the leading end portion of the tube. The present invention contemplates elimination of these drawbacks inherent in conventional endoscope washing apparatus.

SUMMARY OF THE INVENTION

In accordance with the present invention, there is provided an endoscope washing apparatus comprising a grooved member formed with an upwardly open groove, liquid supply means for feeding liquid into the groove, and air injecting means for injecting a multiplicity of streams of air into the liquid in the groove for thereby producing a myriad of foams of air in the liquid in the groove. The groove in the grooved member is preferably so arranged as to extend generally spirally about a vertical axis. The air injecting means may comprise a lower member attached to the underside of the grooved member and forming between the grooved and lower members an air passageway below the groove, the grooved member being further formed with a multiplicity of perforations each providing communication between the groove and the air passageway. In this instance, the liquid supply means of the washing apparatus may comprise a water supply passageway communicable with a source of water, a solution reservoir for storing a chemical solution therein, a solution delivery passageway communicable with the solution reservoir, a water-flow cut-off valve having an inlet port communicating with the water supply passageway, a solution-flow cut-off valve having an inlet port communicating with the solution delivery passageway, and a liquid outlet element located in the neighborhood of one end of the groove, the water-flow cut-off valve and the solution-flow cut-off valve having respective outlet ports which are jointly in communication with the above mentioned liquid outlet element. On the other hand, the air injecting means may comprise a source of air under pressure, an air-flow cut-off valve having an inlet port communicating with the source of air under pressure and an outlet port communicating with the air passageway between the grooved and lower members. As an alternative, the liquid supply means of the washing apparatus according to the present invention may comprise a water supply passageway which is communicable with a source of water, a solution reservoir for storing a chemical solution therein, first and second water-flow cut-off valves having respective inlet ports jointly communicating with the water supply passageway, a liquid outlet element located in the neighborhood of the groove, the first water-flow cut-off valve having an outlet port communicating with the liquid outlet element and the second water-flow cut-off valve having an outlet port communicating with a water/air feed passageway terminating in an outlet fitting, first and second solution feed passageways jointly communicable with the solution reservoir, a solution-flow cut-off valve having an inlet port communicating with the first solution feed passageway and an outlet port communicating with said liquid outlet element, a water/solution/air distribution passageway leading from the second solution feed passageway and terminating in at least one outlet fitting, and a check valve providing one-way communication from the water/air feed passageway to the water/solution/air distribution passageway. In this instance, the air injecting means of the washing apparatus may comprise a source of air under pressure, first and second air-flow cut-off valves having respective inlet ports jointly communicating with the source of air under pressure, the first air-flow cut-off valve having an outlet port communicating with the air passageway between the grooved and lower members and the second air-flow cut-off valve having an outlet port communicating with the water/air feed passageway.

The washing apparatus according to the present invention may further comprise liquid discharge means for allowing liquid to be discharged from each of the groove in the grooved member and the air passageway between the aforesaid grooved and lower members. The liquid discharge means may comprise a liquid discharge passageway communicating with and downwardly leading from the groove, and a liquid discharge valve having an inlet port communicating with the liquid discharge passageway or, as an alternative, main and leakage liquid discharge passageways communicating with and downwardly leading from the groove and the air passageway, respectively, and a liquid discharge valve having an inlet port with which the main liquid discharge passageway is in constant communication and the leakage liquid discharge passageway is communicable.

DESCRIPTION OF THE DRAWINGS

The features and advantages of the endoscope washing apparatus according to the present invention will be more clearly appreciated from the following description taken in conjunction with the accompanying drawings, in which.

DETAILED DESCRUPTION OF THE INVENTION

Figure 1:
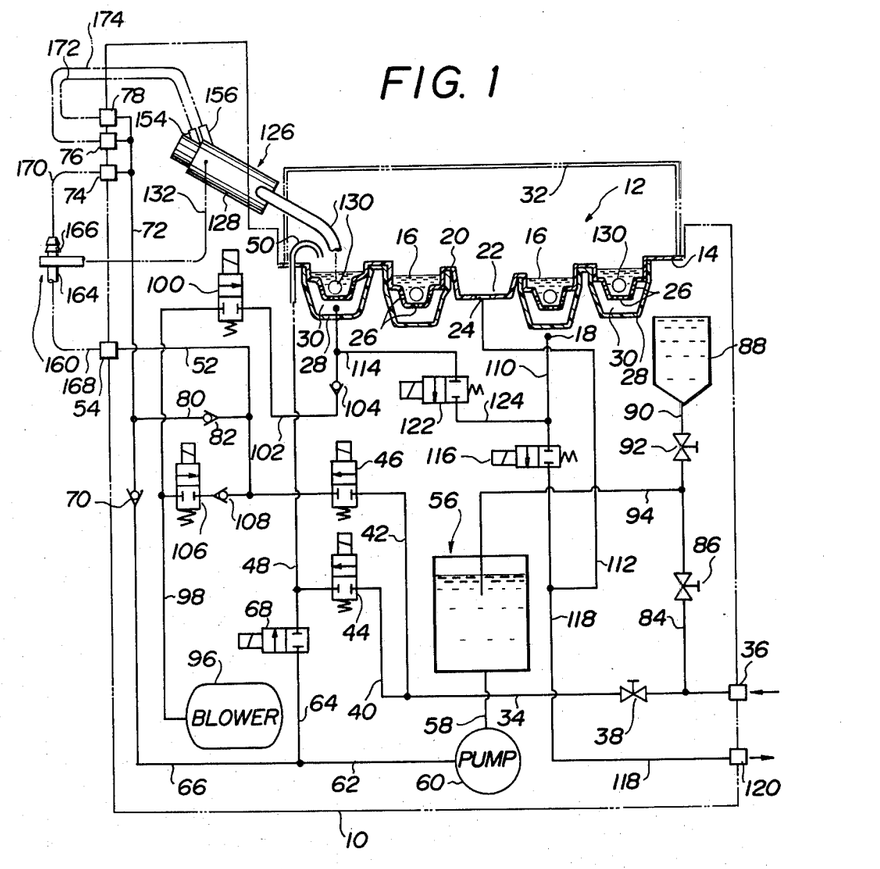
FIG. 1 is a schematic view showing, partially in cross section, a preferred embodiment of the endoscope washing apparatus according to the present invention.
Figure 2:
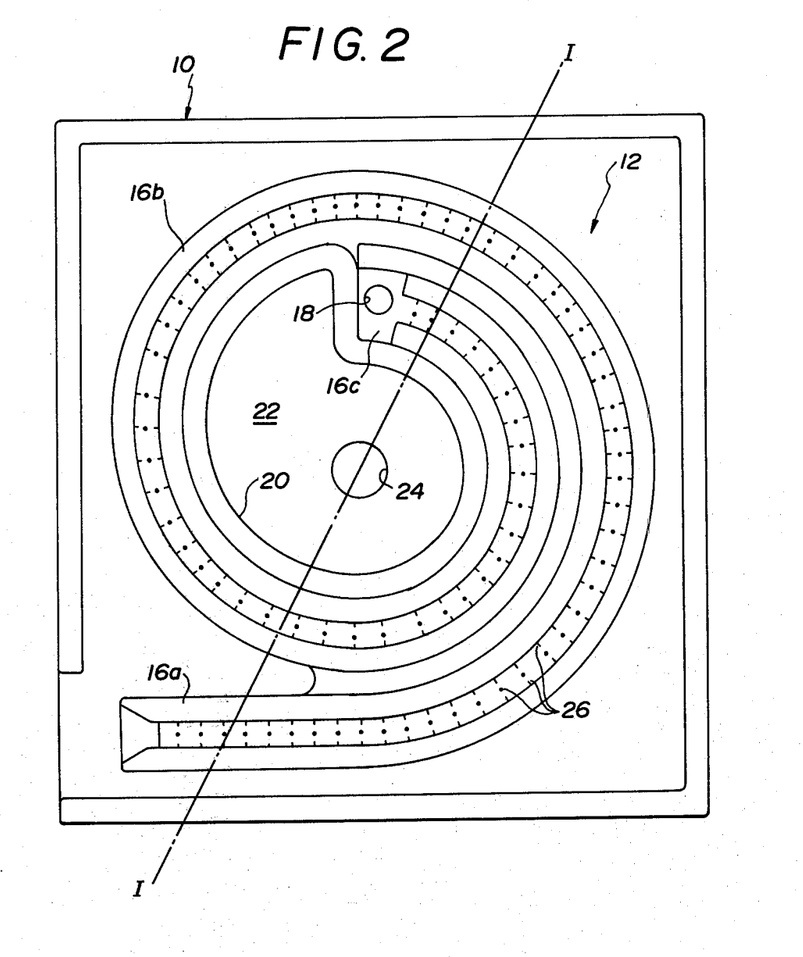
FIG. 2 is a plan view showing a washing basin included in the endoscope washing apparatus illustrated in FIG. 1 in which the washing basin is shown in a cross section taken along line I—I of FIG. 2.

Referring to FIG. 1 of the drawings, an endoscope washing apparatus embodying the present invention comprises a housing structure 10 having a washing basin 12 provided at the top of a main body portion of the housing 10. The washing basin 12 comprises an upper grooved panel 14 formed with a generally spiral groove 16 which has a stepped U-shaped cross section and which is open upwardly throughout its longitudinal extent. As illustrated more clearly in FIG. 2, the spiral groove 16 consists of a substantially straight lead-in end portion 16a and a spiral portion 16b merging out of the lead-in end portion 16a and spirally extending around a certain vertical axis. The spiral portion 16b of the groove 16 terminates in a discharge end portion 16c formed with an opening 18 which constitutes a main liquid discharge port of the washing basin 12. The grooved panel 14 is further formed with a ridge 20 extending in the form of a closed loop inside the spiral portion 16b and defining inside the ridge an upwardly open, central trough 22 which is spatially separate from the groove 16. The grooved panel 14 has formed in its portion thus forming the central trough 20 an opening 24 which constitutes an auxiliary liquid discharge port of the washing basin 12.

The upper grooved panel 14 is further formed with a multiplicity of fine perforations 26 which are open to the spiral groove 16 some upwardly and the others sidewise of the cross section of the groove as will be seen from FIG. 1. The perforations 26 are distributed substantially uniformly throughout the length of the groove 16 and are preferably provided in the ratio of approximately 5,000 perforations per meter with respect of the length of the groove 16. The spiral groove 16 in the embodiment herein shown is assumed to have the length of about 2 meters by way of example and, thus, there are provided approximately ten thousand perforations in the grooved panel 14. Each of the perforations 26 preferably measures about 1 millimeter in diameter. While, furthermore, the spiral groove 16 formed in the grooved panel 14 may extend substantially horizontally, it is preferable that the groove 16 be formed in such a manner as to gradually slope downwardly from the lead-in end portion 16a toward the discharge end portion 16c of the groove 16 as will be seen from FIG. 1. The upper grooved panel 14 may be constructed of any suitable material but is herein assumed to be formed of acrylonitrile-butadiene-styrene resin (ABS resin) by way of example.

The upper grooved panel 14 thus forming part of the washing basin 12 has attached to the underside thereof a lower grooved panel 28 which is formed with a spiral groove extending along and below the spiral groove 16 in the upper grooved panel 14, forming between the respective grooved portions of the panels 14 and 28 a continuous air passageway 30 extending generally spirally between the opposite ends of the spiral groove 16 in the upper grooved panel 14. The air passageway 30 thus formed between the upper and lower grooved panels 14 and 28 is open to the spiral groove 16 in the upper grooved panel 14 through the above mentioned perforations 26 in the panel 14. The lower grooved panel 28 is preferably constructed of a fiberglass-reinforced plastic (FRP) and is bonded to the upper grooved panel 14 by a suitable synthetic resin adhesive. Indicated at 32 in FIG. 1 is a cover for the washing basin 12 thus constructed and arranged. The cover 12 is preferably hingedly connected to the upper end of the main body portion of the housing structure 10 and is adapted to cover the washing basin 12 at the top of the housing structure 10 when the endoscope washing apparatus is in operation.

As is further illustrated in FIG. 1, the housing structure 10 has incorporated therein a fluid or water/solution/air feed system which comprises a water supply conduit 34 leading from a water inlet fitting 36. The water inlet fitting 36 is mounted on the housing structure 10 and is adapted for being releasably connected to a suitable water supply source such as a service water pipe or faucet (not shown). The water supply conduit 34 is provided with a manually-operated water-flow control valve 38 and is branched downstream of the water-flow control valve 38 into first and second water feed conduits 40 and 42 which terminate in the respective inlet ports of first and second solenoid-operated water-flow cut-off valves 44 and 46, respectively. The water-flow control valve 38 is adapted to be manually operated to continuously vary the flow rate of water therethrough between zero and a maximum value. The first solenoid-operated water-flow cut-off valve 44 has an outlet port communicating with a water/solution feed conduit 48 which terminates in a water/solution outlet element or nozzle 50. The water/solution outlet nozzle 50 is mounted on the housing structure 10 and has an outlet end located above and downwardly directed toward the lead-in end portion 16a of the spiral groove 16 in the upper grooved panel 14. On the other hand, the second solenoid-operated water-flow cut-off valve 46 has an outlet port communicating with a water/air feed conduit 52 which terminates in a first outlet fitting 54 mounted on the housing structure 10.

The fluid or water/solution/air feed system incorporated in the housing structure 10 further comprises a solution reservoir 56 positioned below the washing basin 12. The solution reservoir 56 has an outlet conduit 58 which extends from the bottom of the reservoir 56 and which terminates in the suction port (not shown) of a power-driven solution feeding pump 60. The solution feeding pump 60 has a delivery port (not shown) open to a solution delivery conduit 62 which is branched into first and second solution feed conduits 64 and 66. The first solution feed conduit 64 terminates in the inlet port of a solenoid-operated solution-flow cut-off valve 68, the outlet port of which is in communication with the above mentioned water/solution feed conduit 48 leading to the water/solution outlet nozzle 50. On the other hand, the second solution feed conduit 66 communicates through a one-way check valve 70 with a water/solution/air distribution conduit 72 terminating in second, third and fourth outlet fittings 74, 76 and 78 which are arranged in parallel with each other on the housing structure 10. The one-way check valve 70 is adapted to allow fluid to pass from the second solution feed conduit 66 to the water/solution/air distribution conduit 72 through the check valve 70 but prevent the fluid from flowing in a reverse direction through the check valve. The above mentioned water/air feed conduit 52 leading from the outlet port of the second-operated water-flow cut-off valve 46 communicates with the water/solution/air distribution conduit 72 through a branch conduit 80 provided with a one-way check valve 82 which is arranged to allow fluid to pass from the branch conduit 80 to the water/solution/air distribution conduit 72 through the check valve 82 but prevent the fluid from flowing in a reverse direction through the check valve 82.

From the water supply conduit 34 is further branched a third water feed conduit 84 which leads from between the water inlet fitting 36 and the manually-operated water-flow control valve 38 and which is provided with a manually-operated water-flow control valve 86 to be manually operated to continuously vary the flow rate of water therethrough between zero and a maximum value. On the other hand, a liquid storage container or tank 88 is positioned at a level higher than the previously described solution reservoir 56 and has a supply conduit 90 leading from the bottom of the tank 88 and provided with a manually-operated liquid-flow control valve 92 to be manually operated to continuously vary the flow rate of liquid therethrough between zero and a maximum value. The above mentioned third water feed conduit 84 and the supply conduit 90 thus leading from the liquid storage tank 88 are joined together into a mixing conduit 94 which extends downwardly into the solution reservoir 56 and which is open at its leading end in the vicinity of the bottom end of the reservoir 56.

The fluid or water/solution/air feed system of the endoscope washing apparatus embodying the present invention further comprises air feed means for supplying air under pressure into the previously described air passageway 30 formed between the upper and lower grooved panels 14 and 28 constructing the washing basin 12. The air feed means is also incorporated in the housing structure 10 and comprises a power-driven blower unit 96 having a delivery port (not shown) which communicates through an air delivery conduit 98 with the inlet port of a first solenoid-operated air-flow cut-off valve 100. The air-flow cut-off valve 100 in turn has an outlet port communicating with an air feed conduit 102 which terminates in the air passageway 30 in the washing basin 12. The air feed conduit 102 is provided with a oneway check valve 104 which is adapted to allow fluid to pass from the air feed conduit 102 toward the air passageway 30 in the washing basin 12 through the check valve 104 but prevent the fluid from flowing in a reverse direction through the check valve. The air delivery conduit 98 leading from the blower unit 96 is further communicable with the previously described water/solution/air feed conduit 52 through a series combination of a second solinoid-operated air-flow cut-off valve 106 and a one-way check valve 108 which is provided between the air-flow cut-off valve 106 and the water/air feed conduit 52 for allowing air to pass from the air-flow cut-off valve 106 to the water/air feed conduit 52 through the check valve 108 and preventing air from flowing in a reverse direction through the check valve 108.

The housing structure 10 of the endoscope washing apparatus shown in FIG. 1 has further incorporated therein a liquid discharge system for discharging liquid from the washing basin 12 to the outside of the washing apparatus. The liquid discharge system comprises a main liquid discharge conduit 110 leading from the main liquid discharge port 18 of the washing basin 12, an overflow liquid discharge conduit 112 leading from the auxiliary liquid discharge port 24 of the washing basin 12, and a leakage liquid discharge conduit 114 leading from the air feed conduit 102 downstream of the one-way check valve 104 as shown. The main liquid discharge conduit 110 terminates in the inlet port of a first solenoid-operated liquid discharge valve 116 having an outlet port communicating through a waste-liquid outlet conduit 118 with a liquid outlet fitting 120 mounted on the housing structure 10. The overflow liquid discharge conduit 112 is joined to the waste-liquid outlet conduit 118 between the liquid discharge valve 116 and the liquid outlet fitting 120. The leakage liquid discharge conduit 114 terminates in the inlet port of a second solenoid-operated liquid discharge valve 122, the outlet port of which communicates through a conduit 124 with the above mentioned main liquid discharge conduit 110 between the main liquid discharge port 18 of the washing basin 12 and the first solenoid-operated liquid discharge valve 116.

Each of the solenoid-operated valves 44, 46, 68, 100, 106, 116 and 122 in the washing apparatus above described is assumed to be of the type which is open when energized and which is biased by, for example, a suitable spring, to remain in a closed condition when de-energized. It is further assumed herein that the pump 60, blower unit 96 and valves 44, 46, 68, 100, 106, 116 and 122 are electrically connected to a suitable control circuit (not shown) and are sequentially energized in accordance with an automatically timed schedule once the control circuit is actuated by a manually operated main switch (not shown). If desired, however, arrangements may be made so that each of these electrically operated units is actuated by a manually operated switch associated with each of the units so as to be made operative and inoperative by human intervention. Each of the solution reservoir 56 and the liquid storage tank 88 is, furthermore, preferably arranged in such a manner as to be accessible to direct observation from the outside of the housing structure 10 so that the level of the liquid stored therein can be visually inspected from the outside of the washing apparatus during and at the beginning of a washing operation.

While the washing apparatus thus constructed and arranged may be used for the cleaning of any type of optical-fiber endoscopes which are presently known and in use, the description will be hereinafter made on the assumption that the washing apparatus is used for the washing, sterilizing, rinsing and drying of a two-channel gastrofiberscope which is used for the visual examination and photographing of the cavity of a stomach and for the extraction of a cellular tissue of a stomach by means of a forceps.

Figures 3, 4, 6:
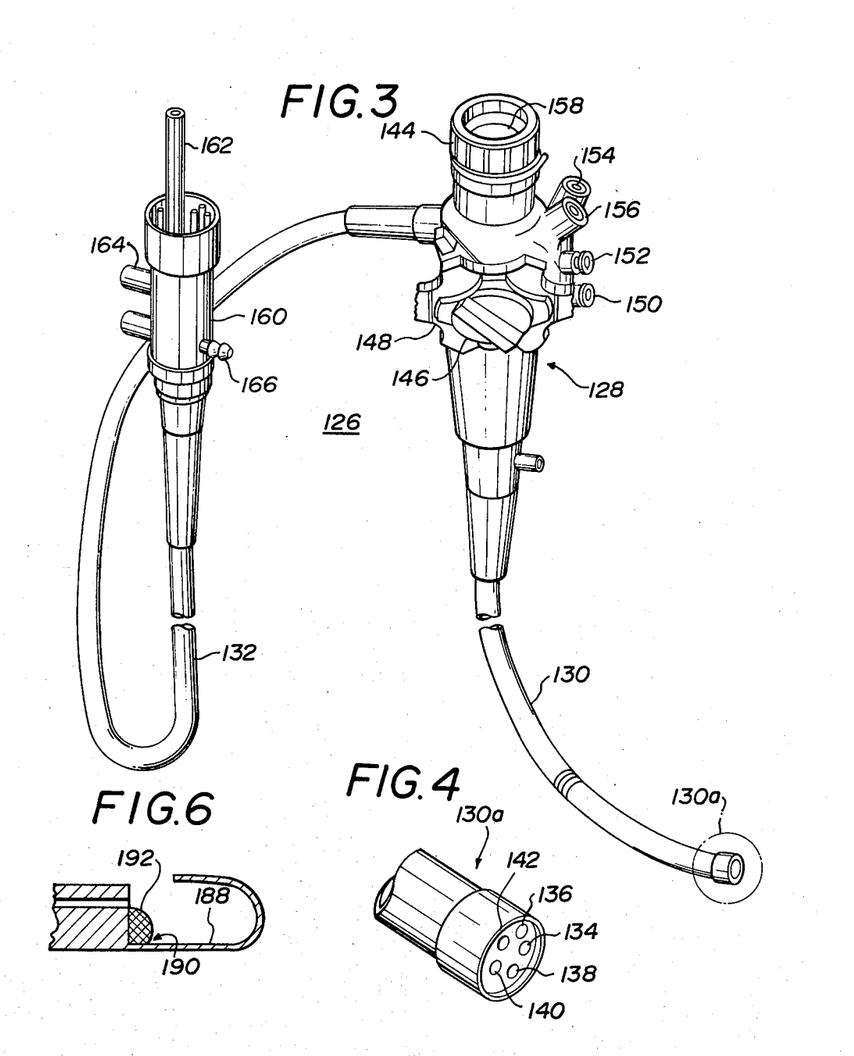
FIG. 3 is a perspective view showing a typical example of a gastrofiberscope which is well known per se.
FIG. 4 is a perspective view showing, to an enlarged scale, a tip portion of the optical-fiber tube forming part of the gastrofiberscope illustrated in FIG. 3.
FIG. 6 is a longitudinal sectional view showing part of a known forceps adapter attached to the optical-fiber tube of an endoscope.

Referring to FIG. 3 of the drawings, a two-channel gastrofiberscope, indicated in its entirety by reference numeral 126, comprises a manipulator unit 128, a flexible optical-fiber tube 130 extending from one end of the manipulator unit 128, and a flexible light-guide tube 132 detachably fitted at one end thereof to the manipulator unit 128. The optical-fiber tube 130 is adapted to be inserted into the cavity of a patient's stomach through his gullet as is well known in the art and is herein assumed, though not shown, to have included therein a bundle of optical fibers for conducting illuminating light therethrough, a bundle of optical fibers for transmitting therethrough an optical image detected in the patient's stomach, an air/water feed conduit for passing therethrough air or water to be injected into the stomach, a suction conduit for passing therethrough the fluid to be sucked in from the stomach, and two conduits each having passed therethrough a flexible line (usually a wire) anchored at its leading end to a suitable forceps (not shown) to be used for holding, seizing or extracting a cellular tissue or any other object in the patient's stomach where desired. The optical-fiber tube 130 thus constructed has at its leading end a tip portion 130a in which the two bundles of the optical fibers in the tube 130 terminate in an objective lens 134 and a light emitter element 136, respectively, as illustrated to an enlarged scale in FIG. 4. As is also shown in FIG. 4, the tip portion 130a of the optical-fiber tube 130 is formed with an air/water outlet opening 138 for the water or air to be injected into the patient's stomach, and two forceps openings 140 and 142 through which the forceps usually retracted into the tip portion 130a of the tube 130 can be selectively moved to project outwardly from the tip portion 130a. Though not shown in the drawings, the tip portion 130a of the optical-fiber tube 130 is further formed with a suction opening communicating with a suction conduit formed in the optical-fiber tube 130 for the fluid to be sucked in from the patient's stomach.

Reverting to FIG. 3, the manipulator unit 128 of the gastrofiberscope 126 has a viewing ring 144 projecting from the opposite end of the manipulator unit 128 to the optical-fiber tube 130 and includes two angle control knobs 146 and 148, a water/air feed push-button 150, a suction control push-button 152, and two forceps manipulator adapters 154 and 156. The viewing ring 144 has an eyepiece 158 and is adapted to directly view the image transmitted through the optical-fiber tube 130 to the eyepiece 158 or to be detachably fitted to a suitable photographing device such as a gastrocamera (not shown). The angle control knobs 146 and 148 are adapted to manually operated to move or orient the tip portion 130a of the optical-fiber tube 130 in two planes which are normal to each other or, for example, upwardly or downwardly and leftwardly or rightwardly. Each of the forceps manipulator adapters 154 and 156 is adapted to have a suitable forceps manipulator (not shown) detachably fitted therethrough to the manipulator unit 128 so that each of the forceps incorporated in the tip portion 130a of the optical-fiber tube 130 inserted into the patient's stomach can be operated to project outwardly from the tip portion 130a into the patient's stomach through the forceps opening 140 or 142 and move in the stomach for various actions to hold, seize or extract a cellular tissue or any other object in the stomach by the manipulative control transmitted to the forceps from the forceps manipulator as is well known in the art.

On the other hand, the light-guide tube 132 leads sidewise from the manipulator unit 128 and terminates in a connector unit 160 including a light guide element 162, an air/water inlet fitting 164 and a suction fitting 166. The light guide element 162 is adapted to be fitted at one end thereof to a suitable source of light such as for example an electric cold-light supply unit (not shown) and is connected at the other end of the element 162 to a bundle of optical fibers incorporated into the light-guide tube 132. The bundle of the optical fibers in the light-guide tube 132 in turn is connected to or merges with the bundle of optical fibers leading through the optical-fiber tube 130 to the light emitter element 136 in the tip portion 130a of the tube 130 so that the light issued from the light source is transmitted through the bundles of optical fibers in the light-guide and optical-fiber tubes 132 and 130 to the light emitter element 136 and emerges outwardly from the light emitter element 136 when the light source is in operation. On the other hand, the air/water inlet fitting 164 and the suction fitting 166 of the connector unit 160 are respectively communicable with the air/water and suction conduits in the optical-fiber tube 130 through air/water feed and suction conduits (not shown) incorporated in the light-guide tube 132 and across valves (not shown) provided in the manipulator unit 128. The previously described air/water feed push-button 150 and suction control push-button 152 are respectively connected to these valves in the manipulator unit 128 so that each of the valves is made open when the associated one of the push-buttons 150 and 152 is manually depressed. The air/water inlet fitting 164 is adapted to be detachably fitted to a suitable source (not shown) of air or water under pressure and further to the previously mentioned first outlet fitting 54 of the endoscope washing apparatus through a suitable conduit 168 as schematically illustrated in FIG. 1, while the suction fitting 166 is adapted to be detachably fitted to a suitable source (not shown) of suction or vacuum and further to the previously mentioned second outlet fitting 74 of the endoscope washing apparatus through a suitable conduit 170 as schematically shown in FIG. 1. The third and fourth outlet fittings 76 and 78 of the endoscope washing apparatus shown in FIG. 1 are adapted to have releasably connected thereto the forceps adapters 154 and 156, respectively, of the manipulator unit 128 of the gastrofiberscope 126 through suitable conduits 172 and 174, respectively, as schematically shown in FIG. 1.

When the gastrofiberscope 126 thus constructed is in use, the optical-fiber tube 130 is inserted into the patient's stomach through his gullet until the tip portion 130a of the tube reaches the cavity of the stomach. To the manipulator unit 128 are fitted suitable forceps manipulators (not shown) through the forceps manipulator adapters 154 and 156 on the manipulator unit 128. On the other hand, the light guide element 162 on the connector unit 160 of the fiberscope 126 is connected to a suitable source (not shown) of light such as a cold-light supply unit so that the light conducted through the optical fiber elements in the flexible light-guide tube 132 and the optical fiber elements in the flexible optical-fiber tube 130 emerges outwardly from the optical-fiber tube 130 through the light emitter element 136 on the tip portion 130a of the tube 130. The air/water inlet fitting 164 on the connector unit 160 is connected to a suitable source of air or water under pressure so that a stream of air or water under pressure is fed through the air/water feed conduits in the light-guide and optical-fiber tubes 132 and 130 and is ejected from the air/water outlet opening 138 in the tip portion 130a of the optical-fiber tube 130 when the air/water feed push-button 150 on the manipulator unit 128 is manually depressed. Furthermore, the suction fitting 166 on the connector unit 160 is connected to a suitable source (not shown) of suction so that a suction or vacuum is developed in the suction conduit in the optical-fiber tube 130 through the suction conduit in the light-guide tube 132 when the suction control push-button 152 on the manipulator unit 128 is manually depressed.

During use of the fiberscope 126, the angle control knobs 146 and 148 on the manipulator unit 128 of the fiberscope 126 are manually operated to move the tip portion 130a of the optical-fiber tube 130 in various directions within the cavity of the patient's stomach in search of a target in the stomach which is illuminated with the light radiated from the light emitter element 136 on the tip portion 130a of the optical-fiber tube 130. The target thus found out in the patient's stomach is visually examined or photographed through the objective lens 134 on the tip portion 130a of the optical-fiber tube 130 and the eyepiece 158 in the viewing ring 144 of the manipulator unit 128 by the aid of the light from the light emitter element 136 on the tip portion 130a of the tube 130. If it is desired to hold, seize or extract a cellular tissue or any other object from the patient's stomach which is being thus visually inspected or photographed, the forceps manipulators fitted to the forceps manipulator adapters 154 and 156 on the manipulator unit 128 are manually operated to project from the tip portion 130a of the optical-fiber tube 130 and to move or bend in various directions within the patient's stomach. If the objective lens 134 or the light emitter element 136 on the tip portion 130a of the optical-fiber tube 130 is contaminated with any foreign substances such as blood or any other humor in the stomach or elsewhere, the air/water feed push-button 154 or the suction control push-button 156 on the manipulator unit 128 is manually operated to blow or wash off the lens 134 or the light emitter element 136 with the stream of air or water injected into the stomach from the air/water outlet opening 138 in the tip portion 130a of the optical-fiber tube 130 or to suck in the contaminant from the lens 134 or the light emitter element 136 into the suction conduit in the optical-fiber tube 130. Not only the outer peripheral surface of the optical-fiber tube 130 inserted into the patient's stomach but the various conduits included in the optical-fiber tube 130 and the light-guide tube 132 are thus subject to contamination during use of the fiberscope 126, the conduits including not only the air/water and suction conduits in the tubes 130 and 132 but the conduits through which the flexible lines or wires connecting the forceps in the tip portion 130a of the tube 130 and the forceps manipulators fitted to the manipulator unit 128.

Description will be hereinafter made regarding the manners in which the gastrofiberscope 126 thus contaminated is washed, sterilized, rinsed and dried sequentially by the use of the endoscope washing apparatus illustrated in FIG. 1.

When the washing apparatus is not in use, the solution feeding pump 60 and the blower unit 96 are maintained de-energized and are thus held inoperative and the solenoid-operated cut-off valves 44, 46, 68, 100, 116 and 122 are maintained de-energized and are accordingly held in closed conditions. Furthermore, each of the manually-operated water-flow control valves 38 and 84 and the manually-operated liquid-flow control valve 92 is held in a fully closed condition thereof. In the liquid storage tank 88 is stored a suitable undiluted or condensed disinfectant or sterilizing solution and in the solution reservoir 56 may be stored a mixture of the solution and water left unused in the preceding cleaning operation. If the diluted solution thus remaining in the solution reservoir appears to be insufficient in volume for the subsequent cleaning operation, desired amounts of undiluted or condensed solution and water may be added to the solution in the reservoir 56 by manually operating the water-flow and liquid-flow control valves 86 and 92.

The gastrofiberscope 126 to be cleaned by the endoscope washing apparatus thus conditioned is fitted to the washing apparatus in such a manner that the manipulator unit 128 thereof is set in a predetermined position on the housing structure 10 as schematically shown in FIG. 1. The air/water inlet fitting 164 and the suction fitting 166 forming part of the connector unit 160 of the gastrofiberscope 126 are connected to the first and second outlet fittings 54 and 74 of the washing apparatus through the conduits 168 and 170, respectively. Likewise, the forceps adapters 154 and 156 forming part of the manipulator unit 128 are connected to the third and fourth outlet fittings 76 and 78 of the washing apparatus. Thus, the air/water inlet fitting 164 of the fiberscope 126 is in communication with the water/air feed conduit 52 of the washing apparatus through the first outlet fitting 54, while the suction fitting 166 and the forceps adapters 154 and 156 of the fiberscope 126 are jointly in communication with the water/solution/air distribution conduit 72 of the washing apparatus through the second, third and fourth outlet fittings 74, 76 and 78, respectively, of the washing apparatus. Though not shown in the drawings, the washing apparatus includes means adapted to maintain the air/water feed and suction control push-buttons 150 and 152 (FIG. 3) of the manipulator unit 128 in the depressed positions thereof when the manipulator unit 128 is set in the predetermined position on the housing structure 10. When the fiberscope 126 is mounted on the washing apparatus, furthermore, the flexible optical-fiber tube 130 leading from the manipulator unit 128 is positioned in the washing basin 12 of the washing apparatus in such a manner as to spirally extend in and along the spiral groove 16 of the washing basin 12 and to have its tip portion 130a located ahead of the discharge end portion 16c of the groove 16.

Before the cleaning operation is started, the water-flow control valve 38 in the water supply conduit 34 is manually operated to provide a desired flow rate of water therethrough so that the water fed from an external source to the water inlet fitting 36 of the washing apparatus is passed through the valve 38 as the desired flow rate when water is allowed to flow through the water supply conduit 34. Throughout operation of the washing apparatus, the manually-operated water-flow and liquid-flow control valves 86 and 92 are kept closed unless it is required to replenish the solution reservoir 56 with an additional mixture of the disinfectant or sterilizing solution and water in the course of the cleaning operation.

When, now, the main switch of the washing apparatus is depressed with the gastrofiberscope 126 set in the predetermined position on the washing apparatus, the first and second solenoid-operated water-flow cut-off valves 44 and 46 are energized to open and simultaneously or immediately thereafter the blower unit 96 is actuated to deliver air under pressure to the air delivery conduit 98. The first solenoid-operated water-flow cut-off valve 44 being made open, the water which has been extended to the inlet port of the valve 44 through the manually-operated water-flow control valve 38 and the water supply conduit 34 is allowed to pass through the water-flow cut-off valve 44 to the water/solution feed conduit 48 and by way of the conduit 48 to the water/solution outlet nozzle 50 which is open above the lead-in end portion 16a of the spiral groove 16 in the washing basin 12. Water is thus continuously ejected from the water/solution outlet nozzle 50 into the spiral groove 16 in the washing basin 12 and produces a continuous stream of water from the lead-in end portion 16a to the discharge end portion 16c of the groove 16 and around the optical-fiber tube 130 longitudinally extending in the groove 16. While water is being continuously supplied from the nozzle 150 to the washing basin 12, air delivered under pressure from the blower unit 96 is passed through the air delivery conduit 98 to the inlet port of the first solenoid-operated air-flow cut-off valve 100 and through the air-flow cut-off valve 100 which is made open and further by way of the air feed conduit 102 and the one-way check valve 104 to the spiral air passageway 30 below the spiral groove 16 in the washing basin 12. The air thus directed into the air passageway 30 of the washing basin 12 is injected into the flow of water in the groove 16 through the perforations 26 formed in the upper grooved panel 14 and forms a myriad of foams of air in the stream of water in the spiral groove 16 in the washing basin 12. The foams thus produced in the water flowing in the spiral groove 16 of the washing basin 12 impinge upon the outer peripheral surface of the optical-fiber tube 130 submerged in the water running in the groove 16 and effectively cause the various foreign substances such as blood and other humors on the outer peripheral surface of the optical-fiber tube 130 to be removed from the tube 130.

The water in the water supply conduit 34 is further passed through the second water feed conduit 42 to the water/air feed conduit 52 past the second solenoid-operated water-flow cut-off valve 46 which is actuated to open concurrently with the first solenoid-operated water-flow cut-off valve 44. The water supplied to the water/air feed conduit 52 is on the one hand passed to the first outlet fitting 54 on the housing structure 10 and on the other hand distributed to the second, third and fourth outlet fittings 74, 76 and 78 on the housing structure 10 by way of the one-way check valve 82, branch conduit 80 and water/solution/air distribution conduit 72. The water passed to the first outlet fitting 54 of the washing apparatus is further directed through the conduit 168 to the air/water inlet fitting 164 on the connector unit 160 of the gastrofiberscope 126 and is passed through the air/water inlet fitting 164 to the air/water conduits in the light-guide and optical-fiber tubes 132 and 130. Likewise, the water passed to the second outlet fitting 74 of the washing apparatus is directed through the conduit 170 to the suction fitting 166 on the connector unit 160 of the gastrofiberscope 126 and is passed through the suction fitting 166 to the suction conduits in the light-guide and optical-fiber tubes 132 and 130. On the other hand, the water which is passed to the third and fourth outlet fittings 76 and 78 of the washing apparatus is directed through the conduits 172 and 174 to the forceps adapters 154 and 156, respectively, on the manipulator unit 128 of the fiberscope 126 and is passed through the forceps adapters 154 and 156 to the conduits through which the flexible lines or wires connected to the forceps in the tip portion 130a of the optical-fiber tube 130 extend. The water thus passed through the various conduits included in the light-guide and optical-fiber tubes 132 and 130 is discharged into the spiral groove 16 in the washing basin 12 through the air/water outlet opening 138, suction opening (not shown) and forceps openings 140 and 142 in the tip portion 130a of the optical-fiber tube 130 shown in FIG. 3. The contaminants or stains which have been remnant in the various passageways included in the gastrofiberscope 126 are, in these manners, forcibly removed from the passageways by the water passed therethrough and are released into the spiral groove 16 of the washing basin 12 together with the water being discharged from the tip portion 130a of the optical-fiber tube 130.

Throughout the washing operation thus conducted, the first and second solenoid-operated liquid discharge valves 116 and 122 are kept de-energized and are accordingly held in the closed conditions thereof. The first solenoid-operated liquid discharge valve 116 being closed, the water supplied to the washing basin 12 from the water/solution outlet nozzle 50 and through the tip portion 130a of the optical-fiber tube 130 as above described overflows from the spiral groove 16 in a little while after the supply of water to the washing basin 12 has been commenced. The water thus overflown from the spiral groove 16 of the washing basin 12 flows beyond the closed-loop ridge 20 of the upper grooved panel 14 into the central trough 22 of the washing basin 12 together with the foreign substances removed from the outer peripheral surface of the optical-fiber tube 130 and the various passageways in the light-guide and optical-fiber tubes 132 and 130. The waste water shed into the central trough 20 of the washing basin 12 is passed through the overflow liquid discharge conduit 112 to the waste-liquid outlet conduit 118 and is discharged from the washing apparatus by way of the liquid outlet fitting 120 attached to the housing structure 10. Throughout the washing operation, furthermore, the second solenoid-operated air-flow cut-off valve 106 is kept de-energized and is accordingly held in the closed condition thereof so that the stream of air delivered from the blower unit 96 to the air delivery conduit 98 is not directed to the water/air feed conduit 52 provided downstream of the air-flow cut-off valve 106.

At a predetermined time interval after the water-flow cut-off valves 44 and 46 and the air-flow cut-off valve 100 have been turned on, the valves 44, 46 and 100 and the blower unit 96 are turned off automatically and, instead thereof, the first and second solenoid-operated liquid discharge valves 116 and 122 are energized to open. The waste, contaminated water in the spiral groove 16 of the washing basin 12 is now allowed to flow through the discharge end portion 16c of the groove 16 to the main liquid discharge conduit 110 and, past the first solenoid-operated liquid discharge valve 116, to the waste-liquid outlet conduit 118. On the other hand, the preforations 26 in the upper grooved panel 14 cause some leaks of water from the spiral groove 16 into the air passageway 30 below the groove 16 especially when the supply of air under pressure into the air passageway 30 is terminated at the end of the washing operation. The water thus admitted into the air passageway 30 is passed through the leakage liquid discharge consuit 114 to the second solenoid-operated liquid discharge valve 122 and, past the valve 122 and by way of the conduit 124, to the first solenoid-operated liquid discharge valve 116 and is also directed to the waste-liquid outlet conduit 118. The water thus passed from the main and leakage liquid discharge conduits 110 and 114 to the waste-liquid outlet conduit 118 is discharged from the washing apparatus through the liquid outlet fitting 36 on the housing structure 10 of the washing apparatus.

Upon lapse of a predetermined period of time after the first and second solenoid-operated liquid discharge valves 116 and 122 are turned on, the valves 116 and 122 are turned off and, in turn, the solution feeding pump 60 and the solenoid-operated solution-flow cut-off valve 68 are energized. The solution feeding pump 60 is now made operative to feed the disinfectant or sterilizing solution from the solution reservoir 56 to the solution delivery conduit 62 and to the first and second solution feed conduits 64 and 64 which are branched from the solution delivery conduit 62. The solution-flow cut-off valve 68 being open, the disinfectant or sterilizing solution directed to the first solution feed conduit 64 is passed through the solution-flow cut-off valve 68 to the water/solution feed conduit 48 and is injected into the spiral groove 16 of the washing basin 12 through the water/solution outlet nozzle 50. A continuous flow of the disinfectant or sterilizing solution is thus produced in the spiral groove 16 of the washing basin 12 and has the optical-fiber tube 130 of the gastrofiberscope 126 submerged therein. On the other hand, the disinfectant or sterilizing solution directed to the second solution feed conduit 66 is passed through the one-way check valve 70 to the water/solution/air distribution conduit 72 and is distributed through the distribution conduit 72 to the second, third and fourth outlet fittings 74, 76 and 78 on the housing structure 10. The solution directed to the second outlet fitting 74 is passed through the conduit 170 to the suction fitting 166 on the connector unit 160 of the gastrofiberscope 126 and further through the suction fitting 166 to the suction conduit in the light-guide tube 132 and the suction conduit in the optical-fiber tube 130. On the other hand, the solution directed to the third and fourth outlet fittings 76 and 78 is passed through the conduits 172 and 174 to the forceps adapters 154 and 156, respectively, on the manipulator unit 128 of the gastrofiberscope 126 and through the forceps adapters 154 and 156 to the conduits passing therethrough the flexible lines or wires connected to the forceps in the tip portion 130a of the optical-fiber tube 130. The disinfectant or sterilizing solution thus passed through the various fluid conducting conduits (except for the conduits leading from the air/water inlet fitting 164 on the connector unit 160) in the fiberscope 126 is discharged into the spiral groove 16 in the washing basin 12 through the openings in the tip portion 130a of the optical-fiber tube 130.

At a predetermined time interval after the sterilizing operation has been started, the solution feeding pump 60 and the solution-flow cut-off valve 68 are de-energized and, in turn, the first and second liquid discharge valves 116 and 122 are turned on. The disinfectant or sterilizing solution which has been stored in the spiral groove 16 in the washing basin 12 and admitted into the air passageway 30 of the washing basin 12 is discharged from the washing apparatus through the liquid discharge valves 116 and 122.

Upon lapse of a predetermined period of time after the discharge of the disinfectant or sterilizing solution has been started, the liquid discharge valves 116 and 122 are de-energized and, in turn, the first and second solenoid-operated water-flow cut-off valves 44 and 46, the blower unit 96 and the first solenoid-operated air-flow cut-off valve 100 are energized so that each of the valves 44, 46 and 100 is made open and the blower unit 96 is made operative to deliver air under pressure to the air delivery conduit 98. Water is for a second time supplied through the water/solution outlet nozzle 50 into the spiral groove 16 in the washing basin 12 and through the first, second, third and fourth outlet fittings 54, 74, 76 and 78 of the washing apparatus and further through the various fluid conducting conduits in the light-guide and optical-fiber tubes 132 and 130 of the fiberscope 126 into the spiral groove 16 in the washing basin 12. Furthermore, the stream of air fed from the blower unit 96 to the air delivery conduit 98 is passed through the first solenoid-operated air-flow cut-off valve 100 and the one-way check valve 104 to the air passageway 30 in the washing basin 12 and is injected through the perforations 26 in the upper grooved panel 14 into the water flowing in the spiral groove 16 in the washing basin 12 as in the case of the first washing operation. Thus, the outer peripheral surface of the optical-fiber tube 130 submerged in the water flowing in the spiral groove 16 is effectively rinsed not only by the flow of water in the groove 16 but by the foams of air produced by the air thus injected into the water through the perforations in the grooved panel 14. On the other hand, the water passed through the various conduits in the light-guide and optical-fiber tubes 132 and 130 washes away the disinfectant or sterilizing solution which has been remnant in the conduits (except for the conduits leading from the air/water inlet fitting 164 on the connector unit 160) in the tubes 132 and 130 of the fiberscope 126.

At a predetermined time interval after the rinsing operation has been started, the valves 44, 46 and 100 and the blower unit 96 are turned off and, in turn, the first and second liquid discharge valves 116 and 122 are energized to open, allowing the water in the spiral groove 16 and the air passageway 30 to be discharged from the washing apparatus through the valves 116 and 122. Upon completion of the discharge of water, the valves 116 and 122 are turned off and, instead thereof, the blower unit 96 and the second solenoid-operated air-flow cut-off valve 106 are energized. The first solenoid-operated air-flow cut-off valve 100 being maintained in the closed condition thereof, the stream of air delivered from the blower unit 96 to the air delivery conduit 98 is passed through the second solenoid-operated air-flow cut-off valve 106 and the one-way check valve 106 to the water/air feed conduit 52 and is distributed on the one hand to the first outlet fitting 54 on the housing structure 10 and on the other hand to the second, third and fourth outlet fittings 74, 76 and 78 on the housing structure 10 by way of the one-way check valve 82 and the water/solution/air distribution conduit 72. The stream of air passed to the first outlet fitting 54 of the washing apparatus is further directed through the conduit 168 to the air/water inlet fitting 164 on the connector unit 160 of the gastrofiberscope 126 and is passed through the air/water inlet fitting 164 to the air/water conduits in the light-guide and optical-fiber tubes 132 and 130. Likewise, the stream of air passed to the second outlet fitting 74 of the washing apparatus is directed through the conduit 170 to the suction fitting 166 on the connector unit 160 of the gastrofiberscope 126 and is passed through the suction fitting 166 to the suction conduits in the light-guide and optical-fiber tubes 132 and 130. On the other hand, the streams of air which are passed to the third and fourth outlet fittings of 76 and 78 washing apparatus are directed by way of the conduits 172 and 174 to the forceps adapters 154 and 156, respectively, on the manipulator unit 128 of the fiberscope 126 and are passed through the forceps adapters 154 and 156 to the conduits having passed therethrough the flexible lines or wires connected to the forceps in the tip portion 130a of the optical-fiber tube 130. The air thus passed through the conduits in the light-guide and optical-fiber tubes 132 and 130 blows off the moisture remnant in the conduits and is discharged together with the moisture through the openings in the tip portion 130a of the optical-fiber tube 130. When the drying operation thus conducted is complete, the blower unit 96 and the second solenoid-operated air-flow cut-off valve 106 are de-energized and put an end to the washing operation for the gastrofiberscope 126.

Figure 5:
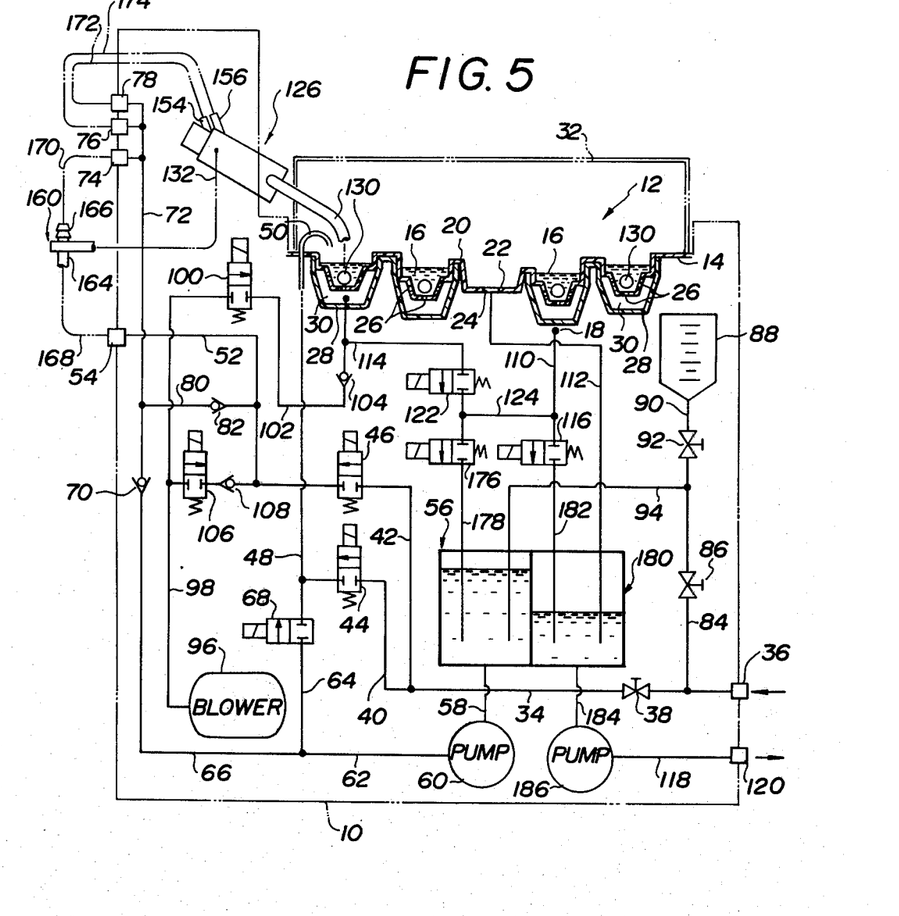
FIG. 5 is a schematic view similar to FIG. 1 but shows another preferred embodiment of the endoscope washing apparatus according to the present invention.

While the disinfectant or sterilizing solution once used is discharged from the washing apparatus through the liquid discharge valves 116 and 122 in the embodiment of FIG. 1, the solution which has been used for the treatment of an endoscope or endoscopes in the washing basin 12 may be recirculated to the solution reservoir 56 for being re-used for the subsequent cleaning operation. FIG. 5 shows an embodiment of an endoscope washing apparatus adapted to achieve such an end.

In the embodiment illustrated in FIG. 5, the conduit 124 leading from the outlet port of the second solenoid-operated liquid flow cut-off valve 122 to the waste liquid discharge conduit 110 communicates with the outlet port of a solution recirculating valve 176 positioned at a level higher than the solution reservoir 56 and lower than the liquid discharge valve 122 as shown. The solution recirculating valve 176 has an outlet port open to a solution recirculating conduit 178 extending downwardly into the solution reservoir 56. On the other hand, the overflow liquid discharge conduit 112 extends downwardly into a waste-liquid storage container or tank 180 positioned below the first solenoid operated liquid discharge valve 116, the outlet port of which is open to a waste-liquid discharge conduit 182 which also extends downwardly into the waste-liquid storage tank 180. A conduit 184 leads from the bottom of the waste liquid storage tank 180 and terminates in the suction port (not shown) of a power driven waste-liquid discharge pump 186 having a delivery port (not shown) communicating through the waste-liquid outlet conduit 118 with the liquid outlet fitting 120 on the housing structure 10. The waste-liquid discharge pump 186 is assumed to be electrically connected to suitable normally-open switch means (not shown) adapted to close when the liquid stored in the waste-liquid storage tank 180 reaches a predetermined level. Such switch means may include a float disposed in the waste-liquid storage tank 180 and mechanically connected to a movable contact element of a normally-open switch, though not shown in the drawings.

At the end of the washing or rinsing operation in which the gastrofiberscope 126 is washed or rinsed with water and foams of air as previously described, the first and second solenoid-operated liquid discharge valves 116 and 122 are energized to open with the solution recirculating valve 176 maintained de-energized and closed. The water which has been stored in the spiral groove 16 of the washing basin 12 is thus passed through the main liquid discharge conduit 110 and past the first solenoid-operated liquid discharge valve 116 to the waste liquid discharge conduit 182 while the water which has leaked into the air passageway 130 from the spiral groove 16 of the washing basin 12 is passed through the leakage liquid discharge conduit 114 and past the second solenoid-operated liquid discharge valve 122 to the conduit 124 and further through the main liquid discharge conduit 110 and the first solenoid-operated liquid discharge valve 116 to the waste-liquid discharge conduit 182. The water thus passed to the waste-liquid discharge conduit 182 is stored in the waste-liquid storage tank 180 until the liquid thus stored in the tank reaches the above mentioned predetermined level. When the predetermined level is reached by the liquid stored in the waste-liquid storage tank 180, the switch means for the waste-liquid discharge pump 186 is closed automatically and actuates the pump 186 to feed the waste-liquid from the tank 180 to the waste-liquid outlet conduit 118 for thereby discharging the waste-liquid from the washing apparatus through the liquid outlet fitting 120 of the washing apparatus. The waste-liquid discharge pump 186 is brought to a stop when the liquid in the waste-liquid storage tank 180 is reduced to the above mentioned predetermined level.

On the other hand, at the end of the sterilizing operation in which the gastrofiberscope 126 is treated with a disinfectant or sterilizing solution, the second liquid discharge valve 122 and the solution recirculating valve 176 are energized to open with the first liquid discharge valve 116 maintained de-energized and closed. The disinfectant or sterilizing solution which has been accumulated in the spiral groove 16 of the washing basin 12 is thus passed through the main liquid discharge conduit 110 and the branch conduit 124 to the inlet port of the solution recirculating valve 176 while the disinfectant or sterilizing solution which has leaked into the air passageway 30 from the spiral groove 16 is passed through the leakage liquid discharge conduit 114 and past the second liquid discharge valve 122 to the inlet port of the solution recirculating valve 176. The disinfectant or sterilizing solution thus directed from the main and leakage liquid discharge conduits 110 and 114 to the inlet port of the solution recirculating valve 176 is passed through the valve 176 and the solution recirculating conduit 178 into the solution reservoir 56 and is for a second time stored in the reservoir 56. If the disinfectant or sterilizing solution stored in the solution reservoir 56 is put to use more than a certain number of times such as, for example, twenty times after the solution has been initially prepared in the reservoir 56, the disinfectant or sterilizing solution becomes deteriorated and may lose its effect. At the end of the sterilizing operation subsequent to the use of the disinfectant or sterilizing solution by such a number of times, therefore, the first and second liquid discharge valves 116 and 122 are energized to open with the solution recirculating valve 122 maintained de-energized. The disinfectant or sterilizing solution in the spiral groove 16 of the washing basin 12 is passed through the first liquid discharge valve 116 into the waste-liquid storaged tank 180, while the disinfectant or sterilizing solution which has leaked into the air passageway 30 of the washing basin 12 is passed through the second and first liquid discharge valves 122 and 116 into the waste-liquid storage tank 180 for being discharged from the tank 180 when the liquid thus stored in the tank reaches the previously mentioned predetermined level. The solution reservoir 56 can be replenished with an additional disinfectant or sterilizing solution by supplying desired amounts of water and undiluted or condensed solution from the third water feed conduit 84 and the liquid storage tank 88 as previously described.

As will have been understood from the foregoing description, the most outstanding feature of the present invention is that, during washing operation, the contaminants and/or stains attached to, for example, the outer peripheral surface of the optical-fiber tube of an endoscope are removed therefrom not only by the flow of water on the outer peripheral surface of the tube but by the attack of a myriad of foams of air which impinge upon the entire outer peripheral surface of the tube. The combined effects of the flow of water on the outer peripheral surface of the optical-fiber tube and the impingement of the foams upon the outer peripheral surface of the tube produce a cleaning efficiency far higher than that usually achievable by a prior-art method in which a jet stream of water discharged from a spray nozzle is sprayed upon the outer peripheral surface of an optical-fiber tube. Since, furthermore, the flow of water and the impingement of the foams occur concurrently throughout the area of the outer peripheral surface of the optical-fiber tube, it takes only about 4 to 5 minutes for the washing of an optical-fiber tube which is about 2 meters long, as compared with about 20 to 25 minutes required for the washing of the same optical-fiber tube in a known method in which a nozzle for the spraying of water upon the tube is moved along the optical-fiber tube from the vicinity of one end of the tube to the vicinity of the other end of the tube. The spray nozzle used in such a prior-art endoscope washing apparatus is arranged to discharge a stream of water at a predetermined angle to the outer peripheral surface of an optical-fiber tube. If, therefore, the optical-fiber tube to be cleaned by the use of the prior-art washing apparatus has in its tip portion a forceps adapter 184 (FIG. 6) formed with a corner portion 186 angled with respect to the direction in which water is to be discharged from the nozzle, it may happen that the stream of the water ejected from the nozzle is not permitted to reach such a corner portion 186 and as a consequence can not remove from the corner portion 186 a mucous or solid matter 190 which may have been deposited in the corner portion 186. Such a problem is not encountered in the endoscope washing apparatus provided by the present invention because of the fact that the optical-fiber tube, for example, of the endoscope being washed by the apparatus is in its entirety submerged into flowing water and is subjected over the entire area of its outer peripheral surface to the attack of foams of air in the flowing water.

While only two preferred embodiments of the endoscope washing apparatus according to the present invention have been described with reference to the drawings, it should be borne in mind that such embodiments are merely illustrative of the subject matter of the present invention and can therefore be modified and/or changed in numerous manners if desired. While, furthermore, it has been assumed that each of the embodiments of the present invention is used for the cleaning of a two-channel gastrofiberscope, it is apparent that an endoscope washing apparatus according to the present invention may be used for the cleaning of any other types of endoscopes such as for example esophago, duodeno, colono, intestinal, gastrointestinal, broncho, naso-pharyngo and vocalchords fiberscopes which are well known per se.

What is claimed is:

1. A washing apparatus for an endoscope including a flexible optical-fiber tube, comprising a grooved member formed with an upwardly open, lengthwise continuous groove, liquid supply means for feeding liquid into said groove, and air injecting means for injecting a multiplicity of streams of air into the liquid in the groove for thereby producing a myriad of foams of air in the liquid in the groove, wherein said air injecting means comprises a lower member attached to the underside of said grooved member and forming between the grooved and lower members an air passageway below said groove, said grooved member being further formed with a multiplicity of perforations each providing communication between said groove and said air passageway, and wherein said liquid supply means comprises a water supply passageway communicable with a source of water, a solution reservoir for storing a chemical solution therein, a solution delivery passageway communicable with said solution reservoir, a water-flow cut-off valve having an inlet port communicating with said water supply passageway, a solution-flow cut-off valve having an inlet port communicating with said solution delivery passageway, and a liquid outlet element located in the neighborhood of one end of said groove, said water-flow cut-off valve and said solution-flow cut-off valve having respective outlet ports which are jointly in communication with said liquid outlet element.

2. A washing apparatus as set forth in claim 1, in which said groove slopes downwardly from one of the opposite ends of the groove to the other.

3. A washing apparatus as set forth in claim 1 or 2, in which said groove extends generally spirally about a vertical axis.

4. A washing apparatus as set forth in claim 3, in which said groove has a lead-in end portion adjacent the spirally outermost end of the groove and a discharge end portion adjacent the other end of the groove and slopes downwardly from the lead-in end portion to the discharge end portion, said liquid supply means comprising a liquid outlet element located in the neighborhood of said lead-in end portion of the groove for injecting liquid into the lead-in end portion.

5. A washing apparatus as set forth in claim 4, in which said grooved panel is further formed with a liquid discharge opening which is open to said discharge end portion of said groove for allowing liquid to be downwardly discharged from the groove through said opening.

6. A washing apparatus as set forth in claim 3, in which said grooved member is further formed with a ridge extending in the form of a closed loop inside the spiral groove and defining within the ridge an upwardly open trough which is separate from the spiral groove across said ridge.

7. A washing apparatus as set forth in claim 6, in which said grooved member is further formed with a liquid discharge opening in said trough for allowing liquid to be downwardly discharged from the trough through said opening.

8. A washing apparatus as set forth in claim 1 or 3, in which said perforations are provided in the ratio of about 5,000 per meter with respect to the length of said spiral groove.

9. A washing apparatus as set forth in claim 1 or 3, in which each of said perforations measures about 1 millimeter in diameter.

10. A washing apparatus as set forth in claim 1 or 2, in which said grooved member is constructed of acrylonirile-butadiene-styrene resin.

11. A washing apparatus as set forth in claim 1, in which said air injecting means comprises a source of air under pressure, an air delivery passageway leading from the source of air, an air-flow cut-off valve having an inlet port communicating with the source of air under pressure and an outlet port communicating with said air passageway between said grooved and lower members.

12. A washing apparatus as set forth in claim 11, in which said air injecting means further comprises a check valve for allowing liquid to be conducted from the outlet port of said air-flow cut-off valve to said air passageway through the check valve and preventing liquid from being conducted in the opposite direction therethrough.

13. A washing apparatus as set forth in claim 11, further comprising liquid discharge means for allowing liquid to be discharged from each of said groove in said grooved member and said air passageway between said grooved and lower member, the liquid discharge means comprising a liquid discharge passageway communicating with and downwardly leading from said groove, and a liquid discharge valve having an inlet port communicating with the liquid discharge passageway.

14. A washing apparatus as set forth in claim 11, further comprising liquid discharge means for allowing liquid to be discharged from each of said groove in said grooved member and said air passageway between said grooved and lower members, the liquid discharge means comprising main and leakage liquid discharge passageways communicating with and downwardly leading from said groove and said air passageway, respectively, and a liquid discharge valve having an inlet port with which said main liquid discharge passageway is in constant communication and said leakage liquid discharge passageway is communicable.

15. A washing apparatus as set forth in claim 14, in which said liquid discharge means further comprises an additional liquid discharge valve provided between said leakage liquid discharge passageway and the inlet port of the first named liquid discharge valve.

16. A washing apparatus as set forth in claim 13 or 14, in which said liquid discharge valve has an outlet port communicating with a waste-liquid outlet passageway open to the outside of the washing apparatus.

17. A washing apparatus as set forth in claim 13 or 14, in which said liquid discharge means further comprises a waste-liquid storage container positioned at a level lower than said liquid discharge valve, and pumping means for forcibly discharging liquid from the waste-liquid storage container to the outside of the washing apparatus, said liquid discharge valve having an outlet port communicating with said waste-liquid storage container.

18. A washing apparatus as set forth in claim 13, further comprising a solution recirculating valve having an inlet port communicating with said liquid discharge passageway and an outlet port communicating downwardly with said solution reservoir.

19. A washing apparatus as set forth in claim 14, further comprising a solution recirculating valve having an inlet port communicating with said liquid discharge passageway and communicable with said leakage liquid discharge passageway and an outlet port communicating downwardly with said solution reservoir.

20. A washing apparatus as set forth in claim 19, in which said liquid discharge means further comprises an additional liquid discharge valve provided between said leakage liquid discharge passageway and the inlet port of the first named liquid discharge valve.

21. A washing apparatus as set forth in claim 1 or 3, in which said liquid supply means comprises a water supply passageway communicable with a source of water, a solution reservoir for storing a chemical solution therein, first and second water-flow cut-off valves having respective inlet ports jointly communicating with said water supply passageway, a liquid outlet element located in the neighborhood of said groove, said first water-flow cut-off valve having an outlet port communicating with said liquid outlet element and said second water-flow cut-off valve having an outlet port communicating with a water/air feed passageway terminating in an outlet fitting, first and second solution feed passageways jointly communicable with said solution reservoir, a solution-flow cut-off valve having an inlet port communicating with said first solution feed passageway and an outlet port communicating with said liquid outlet element, a water/solution/air distribution passageway leading from said second solution feed passageway and terminating in at least one outlet fitting, and a check valve providing one-way communication from said water/air feed passageway to said water/solution/air distribution passageway.

22. A washing apparatus as set forth in claim 21, in which said air injecting means comprises a soucre of air under pressure, first and second air-flow cut-off valves having respective inlet ports jointly communicating with said source of air under pressure, the first air-flow cut-off valve having an outlet port communicating with said air passageway between said grooved and lower members and said second air-flow cut-off valve an outlet port communicating with said water/air feed passageway.

23. A washing apparatus as set forth in claim 22, in which said air injecting means further comprises a check valve providing one-way communication from the outlet port of said first air-flow cut-off valve to said air passageway between said grooved and lower members and a check valve providing one-way communication from the outlet port of said second air-flow cut-off valve to said water/air feed passageway.

* * * * *